United States Patent [19]

Scholl et al.

[11] Patent Number: 5,413,798
[45] Date of Patent: May 9, 1995

[54] PROCESS FOR PREPARING BOVINE PERICARD MATERIALS AND USE THEREOF

[75] Inventors: Edmund Scholl; Helmut Waldert, both of Melsungen; Helmut Beyer, Baunatal, all of Germany

[73] Assignee: B. Braun Melsungen Aktiengesellschaft, Melsungen, Germany

[21] Appl. No.: 223,826

[22] Filed: Apr. 6, 1994

Related U.S. Application Data

[63] Continuation of Ser. No. 52,217, Apr. 22, 1993, abandoned, which is a continuation of Ser. No. 684,675, Apr. 11, 1991, abandoned.

[51] Int. Cl.$^6$ .................... A61K 33/14; A61K 37/12; A61F 2/28
[52] U.S. Cl. .................................... 424/715; 424/722; 424/680; 514/801; 530/356; 623/16
[58] Field of Search ............... 424/423, 715, 722, 680; 623/16; 514/801; 530/356

[56] References Cited

U.S. PATENT DOCUMENTS

| | | | |
|---|---|---|---|
| 4,006,083 | 2/1977 | Westervelt et al. | 210/90 |
| 4,502,159 | 3/1985 | Woodroof et al. | 128/1 R |
| 4,776,853 | 10/1988 | Klement et al. | 623/1 |

*Primary Examiner*—Thurman K. Page
*Assistant Examiner*—Carlos Azpuru
*Attorney, Agent, or Firm*—Fish & Richardson

[57] ABSTRACT

A process for treating bovine pericard tissue to increase resistance to biological degradation by wet-chemical processing, The wet-chemical processing consists essentially of: (i) separating any adherent fat and basal membrane from the tissue; (ii) contacting the tissue with an aqueous, alkaline solution of sodium hydroxide, potassium hydroxide, lithium hydroxide or sodium carbonate to swell the tissue; (iii) contacting the swollen tissue with an aqueous sodium chloride solution to control the swelling; (iv) contacting the tissue with a solution of a metal-ion complexing agent with a pH in excess of 11; and (v) contacting the tissue with an aqueous buffer solution having a pH of 4.5 to 6.0. Each of steps (ii)-(v) is followed by a water rinse. The pericard tissue is then dried and sterilized.

7 Claims, 3 Drawing Sheets

PROCESS FOR PREPARING BOVINE PERICARD MATERIALS AND USE THEREOF

This application is a continuation of application Ser. No. 08/052,217, filed on Apr. 22, 1993, now abandoned, which is a continuation of application Ser. No. 07/684,675, filed Apr. 11, 1991, now abandoned.

The present invention relates to a process for preparing bovine pericard materials having excellent biocompatibility and an increased stability, and to the use of the materials thus prepared as transplants or implants in human medicine and veterinary medicine.

From the beginning of this century it has been attempted in surgery to cover large tissue defects by means of transplants of collagenous connective tissue (Marchant, 1901; Kleinschmidt, 1914). Since 1954 human Dura mater is available as homologous transplant in lyophilized form and since 1973 in the form of a solvent-dried product. In many cases, human Dura, due to its good tissue compatibility, the absence of immunologic reactions and not least its high tensile strength at break has proven its value, so that this biomaterial is successfully used even to-day. Unfortunately, Dura mater, as a human transplant, is available only to a limited extent and, thus, by far cannot meet the demands of surgery. Also there are some indications, for example in neurosurgery and the ear, nose and throat medicine, where Dura transplants frequently have proven to be somewhat to stiff and not the optimum in thickness.

The DE-OS 30 34 273 relates to a method for preparing collagen, said method been characterized in that natural insoluble collagen is treated with an aqueous solution of an alkali sulfate and/or alkali hydroxide, that the fat-free collagen is treated in an aqueous solution containing an alkali sulfate and optionally is washed with water, the collagen is dissolved in an aqueous solution, a small amount of a biologically active substance such as an antibiotic, a hormone or a spermizide is optionally added to the solution, said solution is frozen and the product is dried in vacuo.

However, said Offenlegungsschrift [Public Unexamined Patent Application] does neither anticipate the subject matter of the present invention nor render same obvious to the artisan.

The U.S. Pat. No. 4,006,083 describes a sterile collagen product usable in surgery and having a felt or woven imitation fur structure, which product exerts a hemostatic action, has a high absorption capacity for body liquids, stimulates cell regeneration, has a high resorbability, substantialy is not rejected by body tissues and has optimum mechanical properties, which properties render said product capable of being used in the care of skin injuries or in skin lesions or in bone cavities.

However, the teaching of said U.S. Patent does neither anticipate the subject matter of the present invention nor render same obvious.

The U.S. Pat. No. 4,502,159 describes the preparation of a tubular prosthesis such as, for example, a vessel or ureter prosthesis. Said prosthesis is prepared by suturing the opposite corners of a pericard tissue using a biocompatible suture material. An exact description is provided of the suturing procedure. It is preferred to use bovine pericard which has similar extensibility properties as human tissue. The tubular tissue, once sutured, is tanned in a 0.5% solution of glutardialdehyde for 7 days. The smooth surface of the pericard material has been turned inside, while the basal membranes are on the outer surface. Sterilization is effected by preservation in formalin or by radiation sterilization of a physiological saline containing the pericard.

However, said U.S. Patent does not provide any information on isolation, purification and/or the physical and chemical properties of the tubular prosthesis thus prepared, so that the subject matter of the U.S. Patent cannot render obvious the subject matter of the present invention.

From these circumstances of prior art there arose necessarily a desire to provide a transplant or implant, respectively, which is available to a virtually unlimited extent, which as much as possible includes all of the positive properties of the Dura mater and, in addition thereto, offers some further advantages when handled. Moreover, it should be ensured that no germs dangerous to humans (HIV viruses, hepatitis viruses etc.) could be entrained and introduced by the raw material, as is basically possible with human transplants.

In consideration of all product-relevant parameters, in bovine pericard—also designated as pericard hereinbelow—a biologic material has been found which in an almost optimum manner satisfied the requirements set for an implant for covering human tissue defects.

It is the object of the present invention to create a process for the preparation of bovine pericard materials wherein the biological compatibility and stability of the product obtained thereby is improved. It is a further object of the present invention to provide new possible uses for this product.

Now it has been surprisingly found by experimental research that by means of a modified production process the resistance to biological degradation of the scleroproteins contained in the bovine pericard and the biocompatibility thereof may be enhanced even without an aldehyde tanning procedure using formaldehyde or glutardialdehyde—like those described in the U.S. Pat. No. 4,502,159, WO 84/04669, and in the U.S. Pat. No. 4,456,589.

The present invention relates to a process for preparing bovine pericard material by subjecting raw bovine pericard tissue to operations of wet-chemical processing, oxidative bleaching, washing out, degreasing, drying and sterilizing, said process being characterized in that the wet-chemical processing of the bovine pericard tissue comprises the following steps:

a) Soaking the bovine pericard tissue;

b) Mechanically removing fat tissue and basal membranes from the surface of the bovine pericard tissue;

c) Treating the bovine pericard tissue with a diluted aqueous basic solution;

d) Rinsing the bovine pericard tissue with demineralized water to remove residual base;

e) Treating the bovine pericard tissue with a diluted aqueous sodium chloride solution;

f) Rinsing the bovine pericard tissue with demineralized water to remove residual sodium chloride;

g) Treating the bovine pericard tissue with a complexing agent;

h) Rinsing the bovine pericard tissue with demineralized water to remove residual complexing agent;

i) Treating the bovine pericard tissue with an acidic buffer system; and j) Rinsing the bovine pericard tissue with demineralized water to remove residual acidic buffer system.

BRIEF DESCRIPTION OF THE DRAWINGS

The file of this patent contains at least one photograph executed in color. Copies of this patent with color photographs will be provided by the Patent and Trademark Office upon request and payment of the necessary fee.

Figure 1:
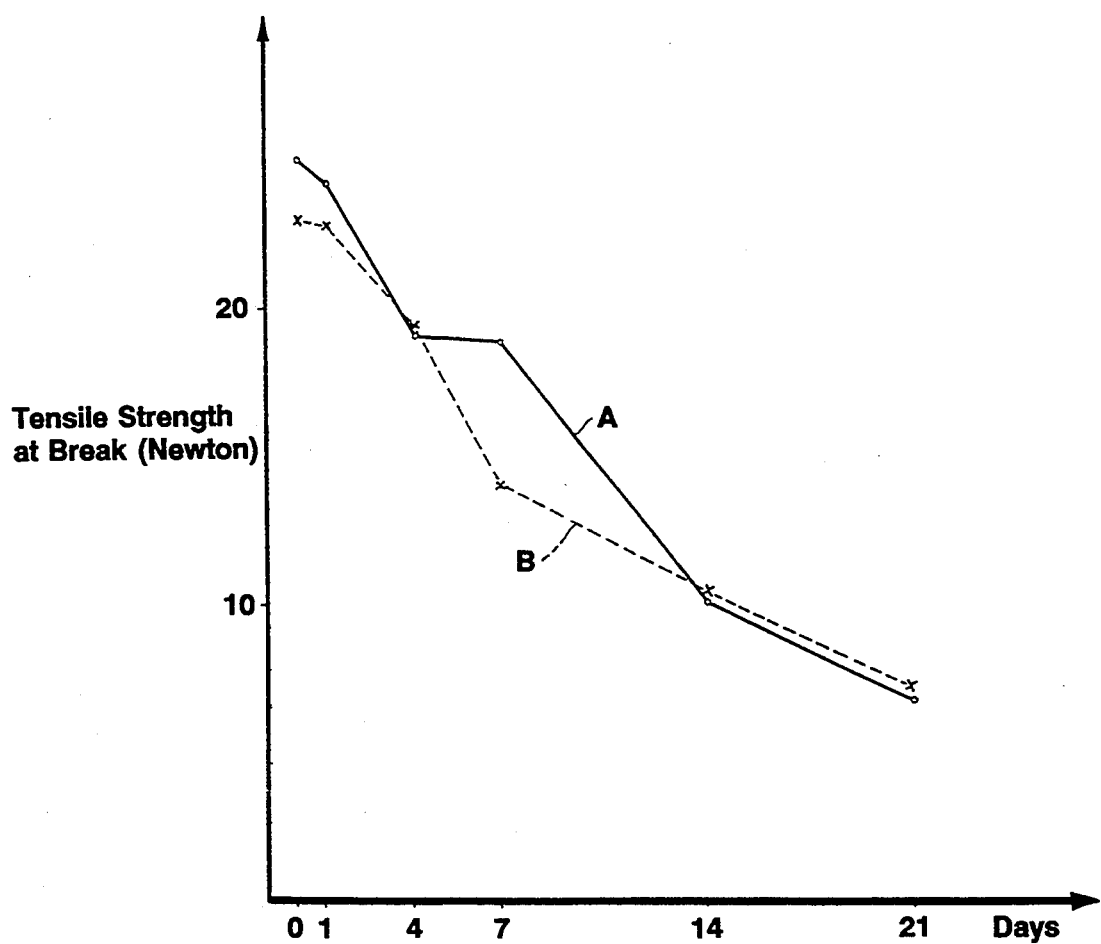
FIG. 1 shows the tensile strength at break vs. time with pericard prepared by the instant invention vs. Lyodura (R).

In a preferred embodiment of the present invention the measure according to feature b) is repeated subsequently to process step d) prior to process step e).

Although the described measures in the wet-chemical processing may be readily carried out above room temperature or below room temperature, it is preferred within the scope of the present invention to conduct all wet-chemical process steps at room temperature, that is between 15° C. and 25° C.

The treatment in process step c) is preferably carried out in a diluted aqueous basic solution of sodium hydroxide, potassium hydroxide, lithium hydroxide and-/or sodium carbonate. Particularly preferred is the use of a 2 to 2.5% by weight aqueous sodium hydroxide solution which generally should act onto the bovine pericard tissue during a period of up to 16 hours, 0.50 to 1.00 liters of the diluted basic solutions being used per 100 grams of bovine pericard tissue. Hereby, on the one hand, a good purification effect is attained which includes a complete deactivation as much as possible of enzymes and potential germs while, on the other hand, damage to the collagen-containing tissue is avoided.

After the treatment with the diluted aqueous basic solution the pericard tissue generally is strongly swollen to 2 to 5 times the initial volume.

The treatment in process step e) is preferably carried out with a 10 to 11% by weight sodium chloride solution, whereby a swelling condition of the collagen may be controlled which is favorable for further processing same. In contrast, lower concentrations in the sodium chloride solution will only cause insufficient de-swelling of the collagen much swollen after the alkaline treatment. Higher sodium chloride concentrations in the solution would cause an unnecessary accumulation to occur of salt remainders in the bovine pericard tissue and are not meaningful already for this reason.

The treatment in process step g) is preferably carried out with a complexing agent as known to the artisan for complexing polyvalent metal ions which in part are present bound to proteins. In this case, a disodium EDTA solution has proven to be particularly preferable, which is present, for example, in a concentration of from 0.3 to 0.5% by weight. Said complexing agent, in order to be able to display its full complexing action, must be adjusted to a basic pH value in excess of 11. The treatment with the complexing agent should in general be carried out over a period of from 0.5 to 2 hours.

It is preferred to continue the rinsing operation in step h) until a weakly alkaline pH value of a maximum of 8.5 will have been reached.

For the treatment in process step i) there is preferably employed, as the acidic buffer system, an acetate buffer system having a pH value of from 4.5 to 6.0.

After the wet-chemical processing operation, the step following thereto of the oxidative bleaching is preferred to be carried out by bleaching the bovine pericard material with an aqueous solution containing hydrogen peroxide in an amount of less than 2% by weight, and particularly of about 1.5% by weight. Said hydrogen peroxide bleaching serves the purpose to oxidatively destroy any accompanying substances of collagen without attacking the collagen itself. It has been shown that hydrogen peroxide concentrations in excess of 2.0% by weight are not suitable within the scope of the invention, since they already cause noticeable damage to the collagen-containing bovine pericard tissue. The hydrogen peroxide treatment is usually carried out during a period from 0.5 to 2 hours, 0.5 to 1.0 liters of the hydrogen peroxide solution being used per 100 g of the bovine pericard tissue.

Subsequently to this operation of oxidative bleaching, residual hydrogen peroxide is removed in a per se known manner by exhaustive washing-out with water.

Degreasing and drying of the bovine pericard tissue are carried out in such a manner that the pieces first are covered with a sufficient amount of acetone, and said solvent is replaced with a new batch 2 to 6 times within a period of from 12 to 24 hours. The bovine pericard tissue having thus been dehydrated is then transferred to a Soxhlet apparatus, and the residual amounts of water and fat are removed by an exhaustive extraction. After the extraction the bovine pericard pieces are air-dried and then re-hydrated in demineralized water (swelling).

Thereafter, the bovine pericard material is lyophilized and sterilized in an automatically controlled freeze-drier.

The preparation process as described hereinabove according to the invention is in a particular manner suitable to produce a product of consistent quality for use in the field of medicine.

The bovine pericard obtained according to the invention may be employed as transplant or implant in various fields of veterinary medicine or human medicine well known to an artisan. In this context, reference may be made to the company brochure "Lyodura$^R$ zum homöoplastischen Ersatz von Körperstrukturen" ["Lyodura$^{(R)}$ for the homoplastic replacement of body structures"] of the company B. Braun Melsungen AG from the year 1978 and the great number of literature references mentioned therein.

Evaluation of the Tensile Strength at Break in the Subcutaneous Implantation Test FIG. 1 shows by way of example which effect can be achieved by the process according to the invention.

FIG. 1 shows the tensile strength at break vs. time of strips 10 mm wide of the pericard material obtained according to the invention and in comparison to that of the product Lyodura$^{(R)}$ well-accepted in the market upon implantation under the dorsal skin of rats (values each averaged for 10 tested animals). In the test, in either case 50 of the strips were implanted and removed after different periods of time passed from the surgery, and the remaining tensile strength at break was measured. Curve A was determined with pericard prepared by the process according to the invention. Curve B was determined with Lyodura(R) for comparison.

Over the observation period of 21 days no significant difference can be determined with respect to the tensile strength at break between the heterologous material pericard prepared according to the invention and the homologous material Lyodura(R); thereby it has been shown that said heterologous material constitutes an excellent substitute for the homologous material.

TABLE

Tensile strength at break of strips of pericard and of Dura (10 mm wide) upon implantation (n = 10 per group); each point entered in the diagram has been based on 10 individual measurements.

| Implantation period (days) | Pericard according to the invention (Newton) | Lyodura(R) (Newton) |
| --- | --- | --- |
| 0 | 25.0 ± 9.4 | 23 ± 10.0 |
|   | 100% ± 38 | 92% ± 40 |
| 1 | 24.1 ± 7.9 | 22.8 ± 9.1 |
|   | 96% ± 32 | 91% ± 36 |
| 4 | 19.0 ± 9.0 | 19.2 ± 8.5 |
|   | 76% ± 36 | 77% ± 34 |
| 7 | 18.8 ± 6.3 | 14 ± 5.1 |
|   | 75% ± 25 | 56% ± 20 |
| 14 | 10.0 ± 4.5 | 10.1 ± 4.5 |
|   | 40% ± 18 | 40% ± 18 |
| 21 | 6.5 ± 3.0 | 7.0 ± 4.5 |
|   | 26% ± 12 | 28% ± 18 |

Second line = value in %
O-Value of pericard = 100%

Evaluation of the Biocompatibility in the Subcutaneous Implantation Test

I.

Subcutaneous implantations of pericard were carried out with altogether 58 rabits and 220 rats. Parameters of the investigation were the pathologic-anatomic findings and the histologic examination of the implants after stagewise periods of time from 7 days up to 12 months.

The pericard implants according to the invention were compared to lyophilized Dura, Lyodura(R) and acetone-dried Dura mater (Tutoplast(R)). The inflammation reaction and the implant condition were macroscopically assessed. Then the samples were fixed in 4% of formalin and subjected to a histologic examination.

The microarchitecture of the collagen skeleton was compared to that of non-implanted controls.

The histologic evaluation of the implants covers the invasion behavior of cells (connective tissue cells, immunocompetent cells), the bond implant-recipient (ingrowth property), resorption and/or vitalization of the alien material and possible rejection reactions.

Results

Upon examination of the devitalized samples prior to the implantation it was determined that same were absolutely free from cells or remainders of cell constituents. On the other hand, lyophilized and, more particularly, solvent-dried Dura mater exhibited some isolated nucleus material.

a) Microarchitecture of the Implants

It could be determined that the arrangement of the collagen fiber structure is important for the immigration behavior of connective tissue cells.

Straight tightly positioned collagen fiber bundles (in solvent-dried Dura) hinder the revitalization. In the pericard and the Lyodura(R) mostly present as dissociated fibers the repopulation with cells from the connective tissue series is facilitated.

b) Vitality of the Implant

The pericard implant behaved as guide rail in the interstices of which the cells immigrate:

Already after one week, plenty of cells have immigrated to the implant which cells have diffusedly spread. They are fibroblasts and histiocytic elements. The vitality index increases from the first to the sixth week.

c) Infiltration of the Implant by Cells not Belonging to the Connective Tissue Series such as Lymphocytes, Macrophages, Alien Body Giant Cells The occurrence of said cells which in the pericard samples unexpectedly occurred at a lower number than in the Dura samples is not to be equated to a beginning rejection reaction, but is to be understood as an immunoinformative process. In contrast to the invasion by fibroblasts and histiocytes, these lymphocytes, macrophages and giant cells seldom deeply penetrate into the implant. Macrophages did more frequently occur where bleeding occurred into the wound bed. The cells (Ly., Macr., GC) were counted, and an index was calculated which in the pericard sample put into clinical use (1.43) was comparatively lower than in the Dura samples (lyophilized: 2.2; acetone-dried: 2.32). This phenomenon is probably due to the fact that pericard is very well devitalized and does not contain any more cell or cell nucleus residues that might possible display an immunogenic action.

d) Acute Inflammation and Rejection Reactions

No immunoreaction was detected in the pericard sample.

In summary it could be determined that the better performance of the pericard samples is due not only to the absence of rejection reactions but also to the better vitality aspect, while here the somewhat lower thickness of the pericard samples plays a role.

II. Evaluation of Biocompatibility and Functionability of Pericard as a Dura Mater Cerebralis Substitute in the Dog The implant, after three and six months post implantationem was well integrated so that it was no longer distinguishable from autochthonous Dura (revitalized by fibrocytes and traversed by blood vessels in the marginal zones). The inner side of the implant is coated with the same cell type as the autologous Dura. Fusions with the cerebral cortex did not exist.

Figure 2:
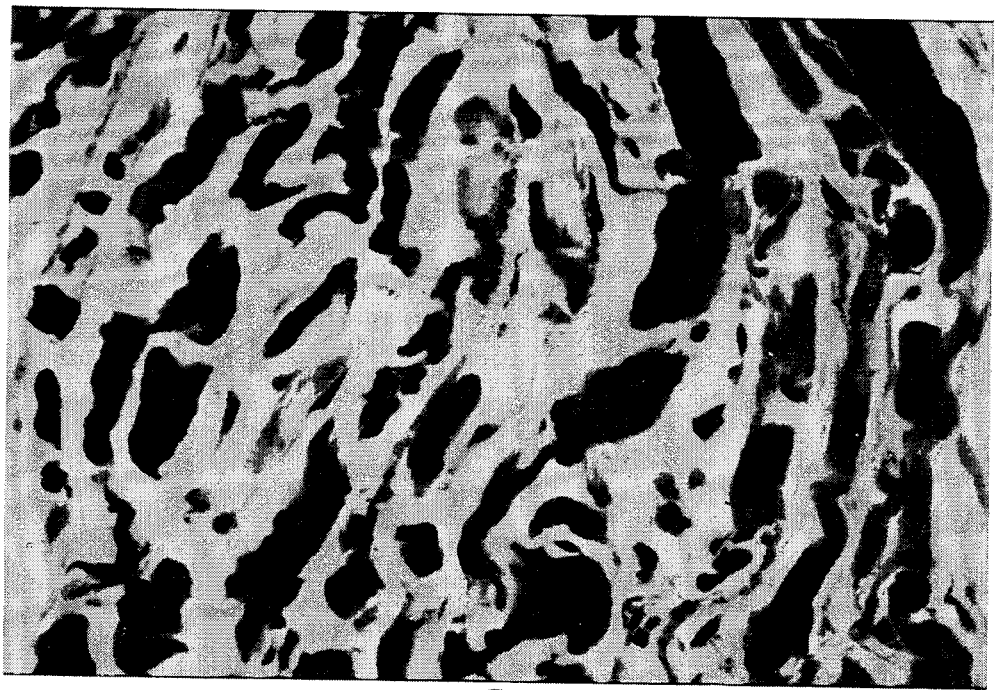
FIG. 2 shows pericard six weeks after subcutaneous implantation.

This effect of the bovine pericard material prepared by the process according to the invention as compared to commercially available Dura materials is documented in the FIGS. 2 to 5 wherein FIG. 2 shows pericard six weeks after subcutaneous implantation to the rat. Well revitalized completely bland implant with vital fibroblasts without lymphocytes; new formation of collagen.

Figure 3:
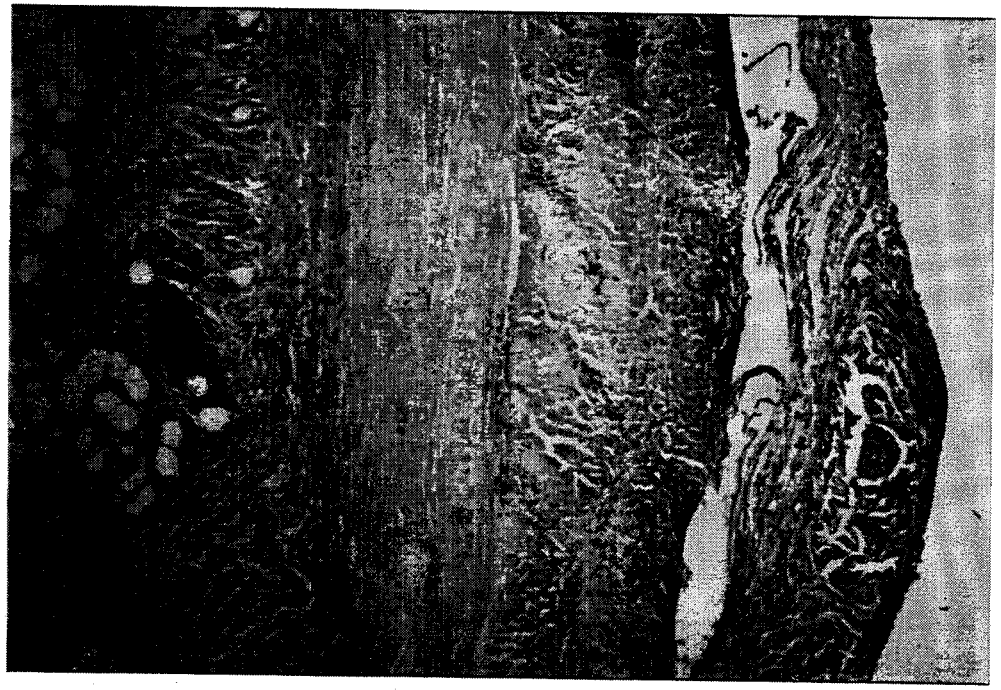
FIG. 3 shows solvent-dried Dura mater six weeks after subcutaneous implantation.

FIG. 3 shows solvent-dried Dura mater six weeks after subcutaneous implantation to the rat (comparison). Local accumulation of lymphocytes; in the central area not yet vitalization with fibroblasts.

Figure 4:
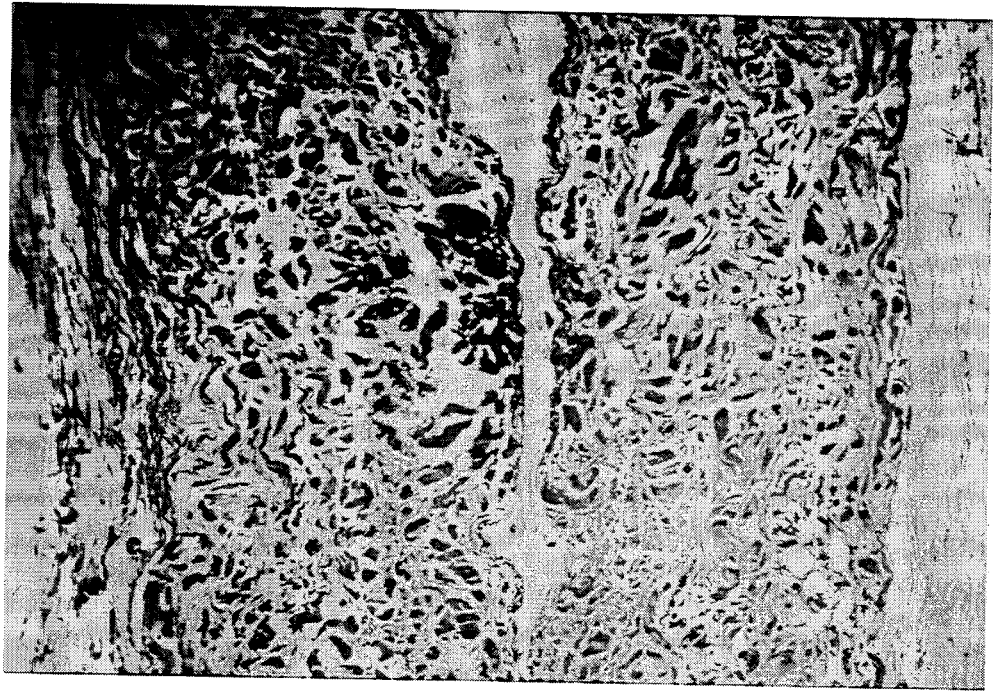
FIG. 4 shows pericard twelve weeks after implantation.

FIG. 4 shows pericard twelve weeks after subcutaneous implantation to the rat. Good integration of implant and host tissue; no immunocompetent cells present.

Figure 5:
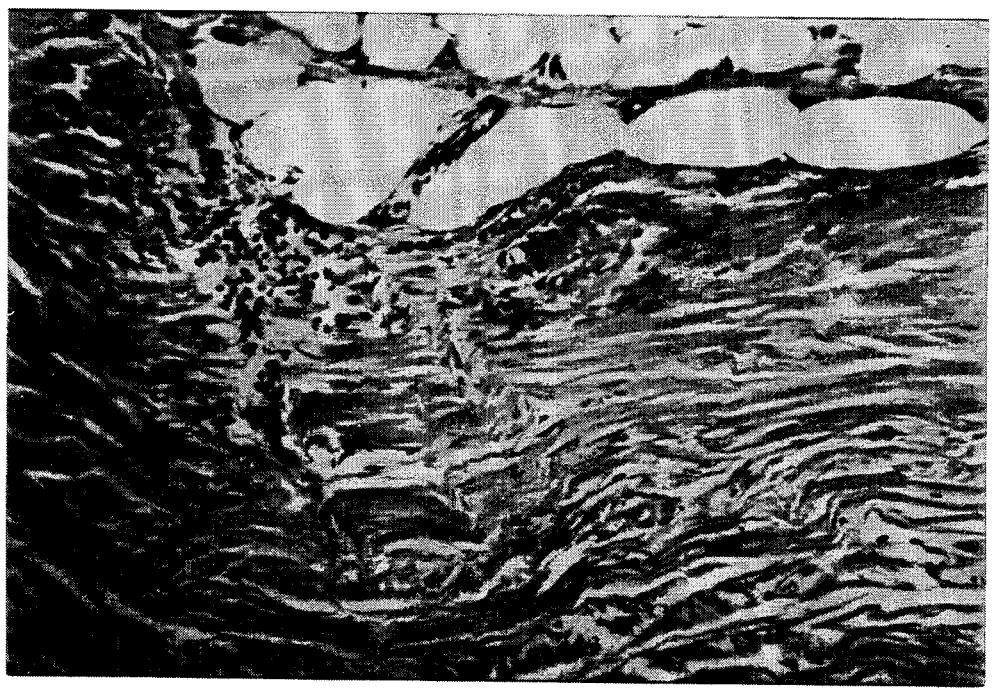
FIG. 5 shows solvent-dried Dura mater twelve weeks p.i. (comparison).

FIG. 5 shows solvent-dried Dura mater twelve weeks p.i. (comparison). Local accumulation of lymphocytes; the implant is mostly avital due to the dense fibrous structure.

The process according to the invention is illustrated hereinbelow by means of a working example for the preparation of the bovine pericard.

Working Example

1. Recovery of the Raw Material

The bovine heart sacs (pericards) employed as the starting material, after the conventional meat inspection by an official veterinarian in the abattoir, first are separated from attached organ parts and grossly rid of fat and connective tissue. Thereby, sheet-like pieces of approximately 30 cm×15 cm in size and a weight of about one kilogram per piece are obtained. The bovine pericards having been thus prepared are transported in a cold bag loaded with ice from the abattoir to the production site and, depending on the amount of the raw material recovered, intermediately stored there at below −20° C. before they are further processed.

2. Wet-chemical processing

The raw pericard pieces first are individually rinsed with purified water—usually soaked with running water—to remove adherent blood and water-soluble protein portions.

After soaking, all macroscopically visible residues of fat tissue and basal membranes are removed. This is followed by a treatment with 2% aqueous sodium hydroxide solution at room temperature. The pericard pieces (5,000 grams) remain in the lye bath (37.5 liters) for a total of 16 hours. The removal therefrom is followed by a rinse process taking about 10 minutes in demineralized water, which process is repeated until the pH of the rinse run-off water has been reduced to below 8. This will be reached after about 1 hour. If any basal membranes and fat remainders will still be observable, then they will be finally removed in this process stage.

The much swollen pericard pieces are now transferred into 37.5 liters of a 10% aqueous saline to adjust the swelling state (partial deswelling) as necessary for the further process steps. The NaCl treatment is carried out at room temperature. It is followed by a rinse process with demineralized water.

In order to remove any interfering heavy metal ions and any possible lime inclusions from the pericard material, the material is then subjected to a treatment with 37.5 liters of a EDTA solution adjusted to be weakly alkaline and having the concentration of 0.3 g in 100 ml. Then, the material is rinsed with demineralized water as in the preceding process steps to remove the excess of complexing agent and at the same time to bring the pH value to 8.5. The one-time treatment now following with 37.5 liters of acetate buffer (pH 4.8; composition, per 100 ml: 59 parts by volume of a solution of 0.01 moles of sodium acetate plus 3 $H_2O$ in 100 ml and 41 parts by volume of 0.01 moles of acetic acid in 100 ml) serves the purpose of buffering all of the residues, if any, left in the pericard tissue and to prepare a weakly acidic medium for the subsequent bleaching operation. Any excessive buffer substances are removed as described above by rinsing with demineralized water.

3. Oxidative Bleaching

Subsequently to the wet-chemical processing, the pericard pieces are subjected to an oxidative bleaching operation taking one hour in 37.5 liters of a 1.5% hydrogen peroxide solution. The bleaching process is carried out, as well as the preceding process steps are, at room temperature. Thereby, on the one hand, the efficiency of the purification operations is ensured while, on the other hand, a deterioration of the collagenous tissue is avoided.

4. Washing Out

In order to remove any excess of reagent, the material is subsequently rinsed with demineralized water according to the conventional regimen.

5. Degreasing

The rinsed bovine pericard pieces are placed in such an amount of acetone that the bovine pericard tissue was completely covered with acetone.

The solvent was three times replaced within 8 hours. The bovine pericard pieces thus dehydrated were then transferred to a Soxhlet apparatus and extracted with acetone for about 8 hours. After the extraction the pericard pieces were air-dried and then re-hydrated in a transportation vessel with demineralized water.

6. Lyophilization

Drying was effected in an automatically controlled freeze dryer. Freeze-drying in detail proceeds as follows:

Lowering the temperature to +1° C., lowering the temperature to −40° C., turning-on the vacuum, heating the trays to +40° C. and drying with full vacuum.

7. Sterilization

Sterilization is effected by radiation sterilization with 2.5 Mrad.

We claim:

1. Process for treating bovine pericard tissue to increase resistance to biological degradation which comprises the steps of:
   (a) wet-chemical processing the pericard tissue by a process consisting essentially of:
      (i) separating from the surface of said tissue any adherent fat and basal membrane,
      (ii) contacting said tissue with a aqueous, alkaline solution of a compound selected from the group consisting of sodium hydroxide, potassium hydroxide, lithium hydroxide and sodium carbonate to swell said tissue and rinsing with water,
      (iii) contacting said swollen tissue with an aqueous sodium chloride solution to control said swelling and rinsing with water,
      (iv) contacting said tissue with a solution of a metal-ion complexing agent with a pH in excess of 11 and rinsing with water, and
      (v) contacting said tissue with an aqueous buffer solution having a pH of 4.5 to 6.0 and rinsing with water;
   (b) drying the pericard tissue; and
   (c) sterilizing the pericard tissue.

2. Process as claimed in claim 1 in which said contacting steps are carried out at room temperature.

3. Process as claimed in claim 1 in which said aqueous sodium chloride solution contains 10–11% sodium chloride.

4. Process as claimed in claim 1 in which the rinsing following contacting with said metal ion complexing agent solution is continued to reduce the pH below 8.5.

5. Process as claimed in claim 1 comprising subsequently contacting said tissue with an aqueous oxidative bleaching solution.

6. Process as claimed in claim 5 comprising subsequently degreasing said tissue.

7. Process as claimed in claim 1 in which said contacting steps are carried out at room temperature, said aqueous alkaline solution comprises 2 to 2.5% sodium hydroxide, said sodium chloride solution contains 10–11% sodium chloride, said metal ion complexing agent comprises disodium EDTA and the rinsing following contacting with said metal ion complexing agent solution is continued to reduce the pH below 8.5.

* * * * *

UNITED STATES PATENT AND TRADEMARK OFFICE
CERTIFICATE OF CORRECTION

PATENT NO. : 5,413,798

DATED : May 9, 1995

INVENTOR(S) : Edmund Scholl et al.

It is certified that error appears in the above-identified patent and that said Letters Patent is hereby corrected as shown below:

Title page, item [30] insert--
German P3835237.0  10/15/88
PCT/EP89/01202    10/11/89 --.

In the abstract, line 3, the comma should be a period.

Col. 5, line 60, after "implants", insert --;--.

Col. 6, line 1, after "implant", insert --;--.

Col. 8, claim 1, line 31, delete "a" and insert --an--.  (our error)

Col. 8, claim 3, line 50, after "chloride" insert --aqueous--.

Signed and Sealed this

Fourth Day of June, 1996

Attest:

BRUCE LEHMAN

*Attesting Officer*    *Commissioner of Patents and Trademarks*